(12) United States Patent
Mackenzie et al.

(10) Patent No.: US 6,692,462 B2
(45) Date of Patent: Feb. 17, 2004

(54) SYSTEM AND METHOD FOR ESTABLISHING VASCULAR ACCESS

(76) Inventors: Andrew J. Mackenzie, 3730 Miramesa Ct. #124, Santa Clara, CA (US) 95051; John E. Carlson, 6088 Glenn Harbor Dr., San Jose, CA (US) 95123

( * ) Notice: Subject to any disclaimer, the term of this patent is extended or adjusted under 35 U.S.C. 154(b) by 70 days.

(21) Appl. No.: 09/735,282

(22) Filed: Dec. 11, 2000

(65) Prior Publication Data

US 2001/0012946 A1 Aug. 9, 2001

Related U.S. Application Data

(63) Continuation-in-part of application No. 09/314,878, filed on May 19, 1999.

(51) Int. Cl.⁷ .................. A61M 27/00; A61M 29/00
(52) U.S. Cl. ................................................ 604/104
(58) Field of Search ........................ 606/191, 192, 606/194, 198; 604/104, 107

(56) References Cited

U.S. PATENT DOCUMENTS

| | | |
|---|---|---|
| 219,296 A | 9/1879 | Naylor, Jr. |
| 319,296 A | 6/1885 | Molesworth |
| 668,879 A | 2/1901 | Miller |
| 702,789 A | 6/1902 | Gibson |
| 2,566,499 A | 9/1951 | Richter |
| 3,788,318 A | 1/1974 | Kim et al. |
| 3,789,852 A | 2/1974 | Kim et al. |
| 3,811,449 A | 5/1974 | Gravlee et al. |
| 3,968,800 A * | 7/1976 | Vilasi ................ 128/207.14 |
| 4,183,102 A | 1/1980 | Guiset |
| 4,320,762 A | 3/1982 | Bentov |
| 4,461,281 A | 7/1984 | Carson |
| 4,493,701 A * | 1/1985 | Bootman et al. ............ 604/73 |
| 4,504,268 A | 3/1985 | Herlitze |
| 4,589,868 A | 5/1986 | Dretler |
| 4,630,609 A | 12/1986 | Chin |
| 4,706,670 A | 11/1987 | Andersen et al. |
| 4,716,901 A | 1/1988 | Jackson et al. |
| 4,846,812 A | 7/1989 | Walker et al. |
| 4,899,729 A | 2/1990 | Gill et al. |
| 4,954,126 A | 9/1990 | Wallsten |
| 4,996,583 A | 2/1991 | Hatada |
| 4,998,539 A | 3/1991 | Delsanti |
| 5,041,093 A | 8/1991 | Chu |
| 5,069,674 A | 12/1991 | Fearnot et al. |
| 5,122,122 A | 6/1992 | Allgood |
| 5,139,511 A | 8/1992 | Gill et al. |
| 5,183,464 A | 2/1993 | Dubrul et al. |
| 5,197,971 A | 3/1993 | Bonutti |
| 5,201,756 A | 4/1993 | Horzewski et al. |
| 5,226,899 A | 7/1993 | Lee et al. |
| 5,230,702 A | 7/1993 | Lindsay et al. |
| 5,234,425 A | 8/1993 | Fogarty et al. |
| 5,246,424 A | 9/1993 | Wilk |
| 5,312,417 A | 5/1994 | Wilk |

(List continued on next page.)

FOREIGN PATENT DOCUMENTS

| | | |
|---|---|---|
| EP | 0 385 920 | 9/1990 |
| WO | WO9819730 | 5/1998 |
| WO | WO9906094 | 2/1999 |

*Primary Examiner*—Kevin T. Truong
*Assistant Examiner*—D. Jacob Davis

(57) ABSTRACT

Systems, kits, and methods for establishing vascular access are described. A system may include a needle, a radially expandable sleeve and a dilator. The methods include creating an initial tissue tract to a target blood vessel with a radially expandable sleeve mounted on a needle. Upon removal of the needle, the dilator is then passed through the radially expandable sleeve to effect radial expansion of the sleeve. Use of the sleeve reduces the risk of injuring tissue surrounding the tissue tract by lessening the axial forces imparted to the tissue. Kits comprise at least the radially expandable sleeve together with instructions for use.

26 Claims, 11 Drawing Sheets

U.S. PATENT DOCUMENTS

| | | | | |
|---|---|---|---|---|
| 5,318,588 | A | 6/1994 | Horzewski et al. | |
| 5,320,611 | A | 6/1994 | Bonutti et al. | |
| 5,380,290 | A | 1/1995 | Makower et al. | |
| 5,431,676 | A | 7/1995 | Dubrul et al. | |
| 5,454,790 | A * | 10/1995 | Dubrul | 604/104 |
| 5,496,292 | A | 3/1996 | Burnham | |
| 4,954,126 | A | 5/1996 | Wallsten | |
| 5,569,200 | A | 10/1996 | Umeno et al. | |
| 5,573,517 | A | 11/1996 | Bonutti et al. | |
| 5,674,240 | A | 10/1997 | Bonutti et al. | |
| 5,814,058 | A | 9/1998 | Carlson et al. | |
| 5,836,913 | A | 11/1998 | Orth et al. | |
| 5,885,217 | A | 3/1999 | Gisselberg et al. | |
| 5,938,587 | A | 8/1999 | Taylor et al. | |
| 5,938,645 | A | 8/1999 | Gordon | |
| 5,961,499 | A | 10/1999 | Bonutti et al. | |
| 6,080,174 | A | 6/2000 | Dubrul et al. | |
| 6,090,072 | A * | 7/2000 | Kratoska et al. | 604/164.01 |
| 6,245,052 | B1 * | 6/2001 | Orth et al. | 604/104 |
| 6,325,812 | B1 | 12/2001 | Dubrul et al. | |
| 6,338,730 | B1 * | 1/2002 | Bonutti et al. | 604/239 |
| 6,450,989 | B2 | 9/2002 | Dubrul et al. | |
| 6,494,893 | B2 | 12/2002 | Dubrul et al. | |
| 2001/0008970 | A1 * | 7/2001 | Ravenscroft et al. | 606/198 |
| 2002/0035373 | A1 * | 3/2002 | Carlson et al. | 606/185 |

* cited by examiner

SYSTEM AND METHOD FOR ESTABLISHING VASCULAR ACCESS

CROSS-REFERENCES TO RELATED APPLICATIONS

This application is a continuation-in-part of and claims the benefit of priority from application Ser. No. 09/314,878, filed on May 19, 1999, the full disclosure of which is incorporated herein by reference.

BACKGROUND OF THE INVENTION

1. Field of the Invention

The present invention relates generally to medical devices and medical methods. In particular, the present invention relates to systems, kits, and techniques for establishing percutaneous vascular access.

Access to patient blood vessels is necessary for a wide variety of diagnostic and therapeutic purposes. For example, intravascular catheters are introduced to both the arterial vasculature and the venous vasculature, typically using either surgical cut down techniques or percutaneous introduction techniques. Of particular interest to the present invention, the most common percutaneous introduction technique is referred to as the Seldinger technique. While a wide variety of variations exist, the basic Seldinger technique relies on initially accessing a target blood vessel with a needle. A guidewire is then passed through the needle into the blood vessel, and the needle withdrawn over the guidewire. A dilator is then passed over a guidewire to enlarge the diameter of the tissue tract so that it can accommodate a larger introducer sheath. Once the introducer sheath is in place, access to the blood vessel can be reliably obtained through a lumen of the sheath.

With the introduction of a greater number and variety of intravascular techniques, including angioplasty, atherectomy, endovascular aneurysm repair, minimally invasive cardiac surgery, and the like, a need has arisen to provide relatively large diameter access to the vasculature. Thus, access sheaths having a diameter of 24 French (8 mm) or greater are now commonly introduced using the Seldinger or other percutaneous techniques. As the number and size of procedures increase, so does the risk of complications which place individual patients at risk and which are costly to the healthcare system.

As larger and larger access diameters are sought, the need to dilate the tissue tract becomes greater. The use of conventional dilators, however, can significantly traumatize the skin. In particular, advancement of a conventional dilator through a tissue tract exerts significant axial forces on the tissue, potentially causing injury and delamination of adjacent tissue layers.

For these reasons, it would be desirable to provide improved systems, kits, and methods for establishing percutaneous vascular access for catheterization and other vascular procedures. In particular, it would be desirable to provide vascular access techniques which could dilate a percutaneous tissue tract with minimum trauma to tissue surrounding the tract. Such techniques should be suitable for forming large (as well as small) diameter access channels, typically having diameters as large as 6 mm, preferably as large as 8 mm, or larger. It would be still further desirable if the improved systems, kits, and methods would require little modification of existing techniques and systems for establishing vascular access. At least some of these objectives will be met by the inventions described hereinafter.

2. Description of the Background Art

The use of radially expanding dilators for accessing non-vascular body locations is described in U.S. Pat. Nos. 5,814,058; 5,431,676, 5,183,464, and copending application Ser. No. 08/424,696, all of which are commonly assigned with the present application and the full disclosures of which are incorporated herein by reference. U.S. Pat. No. 5,230,705, describes use of a needle disposed within a dilation structure for use in intravenous catheterization. See also U.S. Pat. Nos. 5,312,417; 5,246,424; 5,201,756, 5,139,511, and 4,899,729.

SUMMARY OF THE INVENTION

The present invention provides improved systems, kits, and methods for establishing percutaneous access to a patient's vasculature. Access can be established to a variety of particular blood vessels, including both arteries and veins, such as the femoral artery, radial artery, and the like. The purpose for accessing the vasculature can be diagnostic, such as angiography, intravascular ultrasound, cardiac mapping, or the like, or can be therapeutic, such as angioplasty, atherectomy, minimally invasive cardiac surgeries, endovascular aneurysm repair, cardiac ablation, or the like.

The methods of the present invention comprise particular improvements over the Seldinger technique, as described above, employing a sheath dilator for expanding an initial needle penetration to a target blood vessel. As set forth in the Background section, use of a dilator/sheath assembly directly within a tissue tract can subject the tissue to significant axial forces which can delaminate or otherwise damage the tissue surrounding the tissue tract. The present invention reduces the risk of injuring the tissue by introducing a radially expandable sleeve over a guidewire which has been placed through the tissue tract using otherwise conventional techniques. The radially expandable sleeve will be immobilized (typically being manually held) relative to the tissue tract so that axial advancement of a sheath/dilator or other dilating member through the radially expandable sleeve will impart little or no axial force to the underlying tissue. Instead, only radially expansive forces will be transmitted outwardly through the sleeve.

Systems according to the present invention for establishing vascular access over a guidewire comprise a dilator and a radially expandable sleeve. The dilator has a lumen sized to be introduced over the guidewire. The guidewire will have a pre-selected diameter which is generally constant over its entire length. The diameter will be relatively small, typically being either 0.36 mm (0.014 in.) or 0.89 mm (0.035 in.), which are conventional sizes for guidewires used for vascular access. The lumen of the dilator will be sized slightly greater than the outside diameter of the guidewire with which it is to be used, typically being 0.46 mm (0.018 in.) or 1 mm (0.4 in.) for each of the guidewire sizes mentioned above. The dilator will have an outside diameter selected to provide for a desired degree of radial expansion of the tissue tract. Typically, the outside diameter of the dilator will be in the range from 1 mm to 2.5 mm for the smaller guidewire size and 1.3 mm to 3.3 mm for the larger guidewire size.

The radially expandable sleeve will have a lumen therethrough and an unexpanded diameter which is only slightly greater than the diameter of the associated guidewire, e.g., 0.41 mm (0.016 in.) for the 0.36 mm (0.014 in.) guidewire and 0.96 mm (0.038 in.) for the 0.89 mm (0.035 in.) guidewire. Typically, the sleeve will have an outside diameter which is no more than 300% of the guidewire diameter, preferably being no more than 200% of the guidewire diameter. The sleeve, however, will have an expandable outer wall which permits the dilator to be introduced over the guidewire and through the sleeve to cause expansion. In a first embodiment, the outer wall of the radially expandable sleeve can be compliant or elastic so that its cross-section collapses after expansion if the dilator used for expansion is withdrawn. Typically, the compliant or elastic structure will be reinforced with a tubular braid, e.g., a braid formed as a mesh of non-elastic filaments where radial expansion will cause axial shortening of the braid. The braid may be embedded in the elastic or compliant layer or may be covered by the elastic or compliant layer.

Alternatively, the radially expandable sleeve may have a plastically deformable body or may comprise a locking structure so that it retains its expanded diameter after dilation. Typically, the plastically deformable radially expandable sleeves will also be reinforced with the braid. For example, the braid may be covered or impregnated with a suitable plastically deformable material, such as expanded PTFE, irradiated polyesters, and the like. As an alternative or an addition to use of the plastically deformable sleeve matrix, the braid reinforcement may be configured so that the braid filaments interlock upon radial expansion. Thus, the filaments in themselves will resist radial collapse after the sleeve has been expanded.

When the system employs an elastic or compliant radially expandable sleeve, it will be necessary to provide further system component(s) to retain the sleeve in its expanded configuration after the dilator has effected dilation. Conveniently, this can be accomplished using a conventional sheath/dilator assembly as the dilator. After the sleeve has been expanded (thus expanding the tissue tract), an inner portion of the assembly, usually referred to as the dilator, can be withdrawn from the sheath, leaving the sheath in place to maintain the expanded diameter of the tissue tract. While this is an effective approach and utilizes a device with which the treating physician is quite familiar, it has the disadvantage that the radially expandable sleeve adds a very small thickness to the diameter to which the tissue tract is expanded. Use of the plastically deformable or locking sleeve will, in contrast, allow use of a simple dilator, i.e., one without an associated sheath. Thus, there will be no additional structure and no need to dilate the tissue tract any more than would be required with a conventional sheath dilator.

Optionally, the system may further comprise a sleeve introducer adapted to facilitate introduction of the sleeve over a guidewire through the tissue tract. In some patients, conventional Seldinger and other access techniques can be difficult due to the presence of scar tissue or other complicating factors. In such cases, significant pushing force may be required to advance the sleeve over the guidewire. While the small profile of the introducer sleeve reduces the force necessary for introduction over the guidewire, in some cases it will be desirable to still further reduce the introduction force. Such a reduction in introduction force can be accomplished by providing a tapered distal tip on the sleeve. While this could be done by modifying the design of the sleeve itself, it is more easily accomplished using a separate introducer sleeve having a tapered distal end a lumen therethrough. The sleeve is configured to receive a guidewire through its lumen and to be received within the lumen of the radially expandable sleeve. By then placing the radially expandable sleeve over the sleeve introducer, the temporary assembly of the sleeve and sleeve introducer can be introduced over the guidewire so that the tapered end of the sleeve introducer first advances through and dilates the tissue tract to reduce the necessary introduction force. After the distal end of the assembly reaches the blood vessel, the dilator may then be introduced over the assembly, i.e., the lumen of the dilator will pass over the exterior of the sleeve introducer. After dilation of the radially expansible sleeve is accomplished, the sleeve introducer and guidewire can then be removed from the expanded access channel defined by the dilator.

Methods according to the present invention for establishing vascular access comprise forming a percutaneous tissue tract to a target blood vessel. Typically, the tissue tract is initially formed using a needle and guidewire according to conventional techniques, such as the first steps in a Seldinger access protocol. A guidewire is positioned in the tissue tract, and a radially expandable sleeve positioned over the guidewire and through the tissue tract so that a distal end of the sleeve lies in the blood vessel. A proximal end of the sleeve will remain outside the tissue tract, and the sleeve may then be expanded from a narrow diameter configuration to a larger diameter configuration to provide an access lumen to the blood vessel. In a first embodiment, the sleeve will be plastically deformable or otherwise capable of maintaining its larger diameter configuration, and expansion can be effected using a simple dilator without an associated sheath. In an alternative embodiment, the radially expandable sleeve will be elastic or compliant and expansion can be effected using a sheath dilator where the dilator is removed after expansion and the sheath left in place to maintain the desired access lumen. Usually, the radially expandable sleeve which is advanced over the guidewire will have an outer diameter which is no more than 300% larger than the guidewire diameter, preferably no more than 200% larger.

The present invention still further provides kits for performing any of the methods described herein. The kits will comprise at least a radially expandable sleeve together with instructions setting forth a method according to the present invention. Usually, the kits will further comprise a dilator and optionally still further comprise a guidewire. The dilator may be a simple dilator with no associated access sheath when the radially expandable sleeve is plastically deformable or otherwise capable of maintaining its expanded diameter configuration. Alternatively, the dilator can be a conventional sheath/dilator combination when the radially expandable sleeve is elastic or compliant.

DESCRIPTION OF THE SPECIFIC EMBODIMENTS

Figure 1:
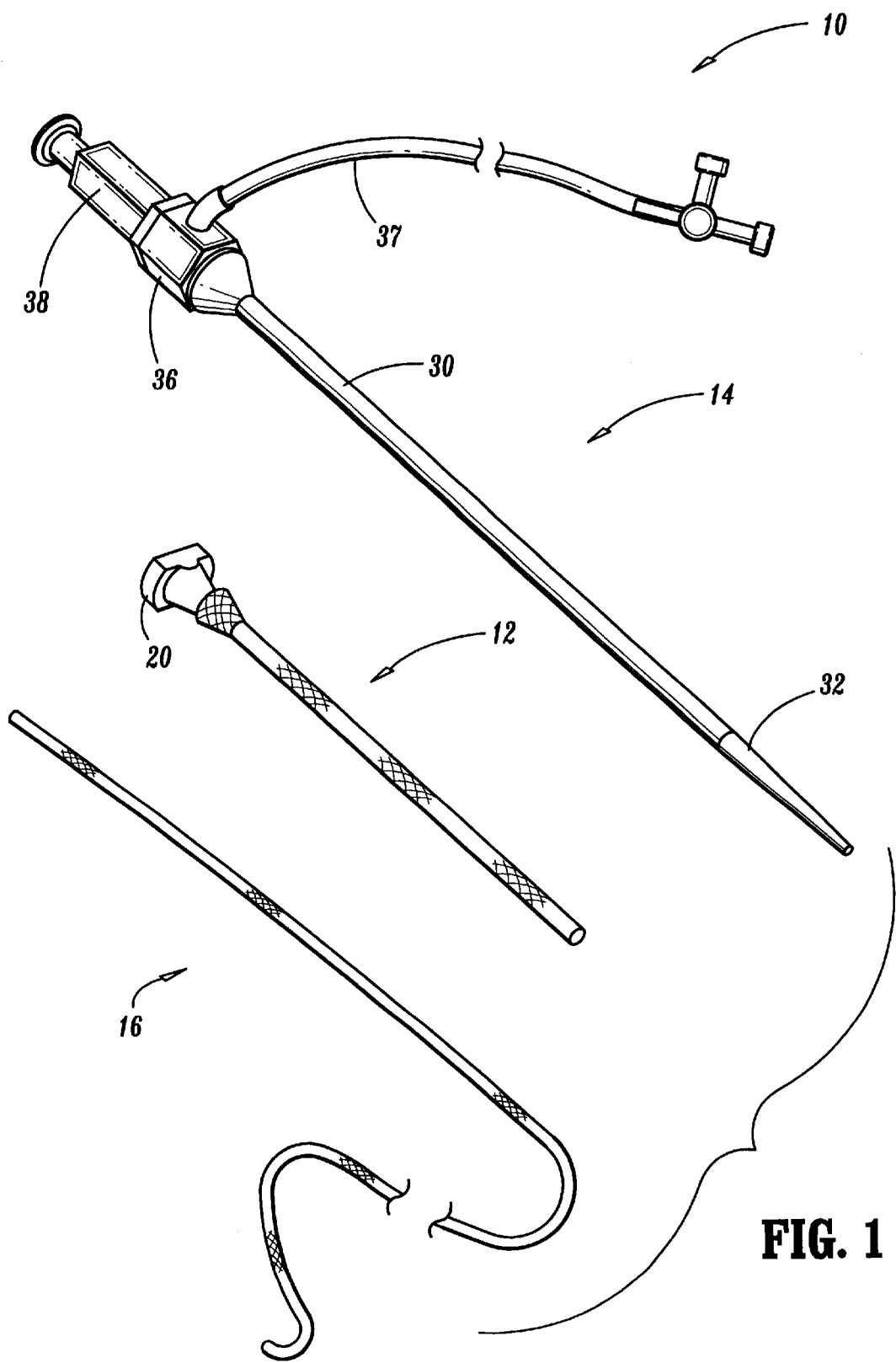
FIG. 1 illustrates a system comprising a radially expandable sleeve, a dilator, and a guidewire, according to the present invention.

Referring to FIG. 1, a system 10 for establishing vascular access according to the principles of the present invention comprises a radially expandable sleeve 12, a dilator 14, and a guidewire 16. The radially expandable sleeve comprises a radially expandable tubular body having a proximal end, a distal end, and an axial lumen extending from the proximal end to the distal end. Usually, a handle 20 is provided at the proximal end of the body so that the sleeve can be manually held during use, e.g., tension can be applied on the handle as the dilator 14 is passed through the body of the sleeve as described in more detail below. The radially expandable sleeve 12 may have a compliant or elastic structure which permits expansion from an initial small diameter (radially collapsed) configuration to a larger diameter configuration which is caused by introduction of the dilator therethrough. Use of the compliant or elastic sleeve will require a separate component for maintaining the expanded diameter of the tissue tract, as described in more detail below. Alternatively, the radially expandable sleeve can have a plastic or other locking structure so that, once expanded, it will retain its large diameter configuration without the need for using other supports, devices, or the like.

An exemplary radially expandable sleeve comprises an expandable tubular braid which is initially an elongated, narrow-diameter configuration. The braid may be open, but will usually be laminated or covered with a coating or layer of elastic or plastically deformable material, such as silicone rubber, latex, polyethylene, urethane, C-flex, or the like. The braid is preferably formed as a mesh of individual non-elastic filaments, such as polyamide fibers, polyester, stainless steel, or the like. The specific structures for forming such radially expandable sleeves are described in U.S. Pat. No. 5,814,058, a full disclosure of which has previously been incorporated herein by reference.

Exemplary sleeve diameters have been set forth above. Usually, the sleeve will have a length in the range from 3 cm to 30 cm, more usually from 10 cm to 25 cm. The exact dimensions of the sleeve will depend on the desired use and location of the target blood vessel to be accessed.

A dilator 14 may be a simple dilator having a tapered distal end and smooth transition to a uniform body diameter. The dilator will have a guidewire lumen to permit introduction over the guidewire and through the radially expandable sleeve, as described in more detail below. As illustrated, dilator 14 is in the form of a conventional sheath/dilator assembly of the type which is commercially available from vendors, such as Bard Cardiology, Billerica, Mass., under the trade name Input™. The dilator/sheath assembly includes an outer sheath 30 with an inner tapered dilator 32 which is removable from the sheath. The sheath has a hemostatic valve 36 at its distal end and a side access tube 37 which permits perfusion or aspiration through the lumen of the sheath. The dilator 32 has a handle 38 at its proximal end and an internal lumen which permits introduction over the guidewire 16. The guidewire 16 may be a conventional vascular access guidewire, typically having a diameter of either 0.36 mm (0.014 in.) or 0.89 mm (0.035 in.), and a length in the range from 35 cm to 100 cm.

Figure 2A:
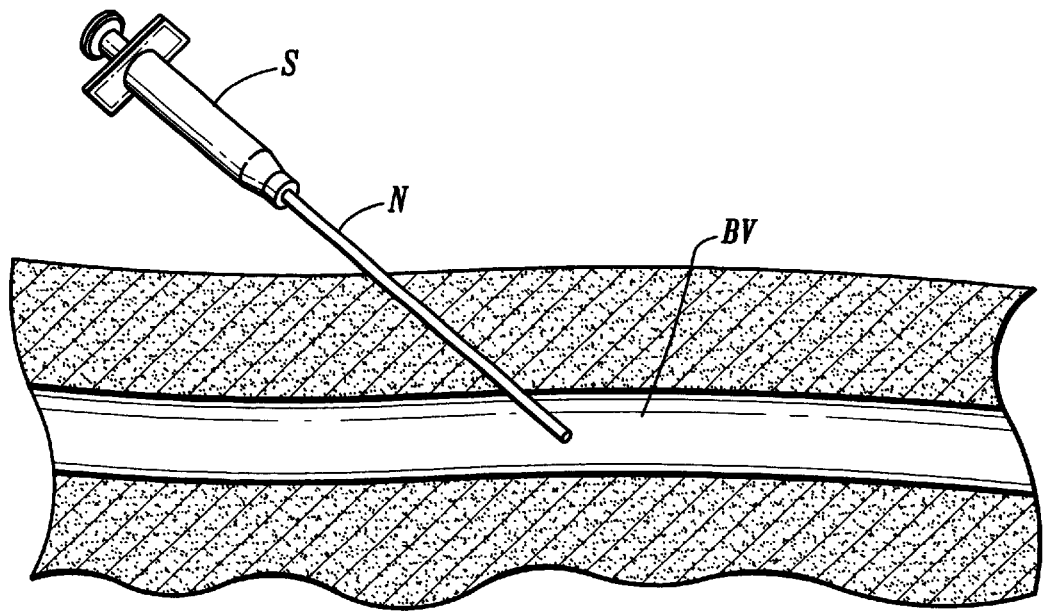
FIGS. 2A–2E illustrate use of the system of FIG. 1 for establishing vascular access to a target blood vessel according to a method of the present invention.
Figure 2B:
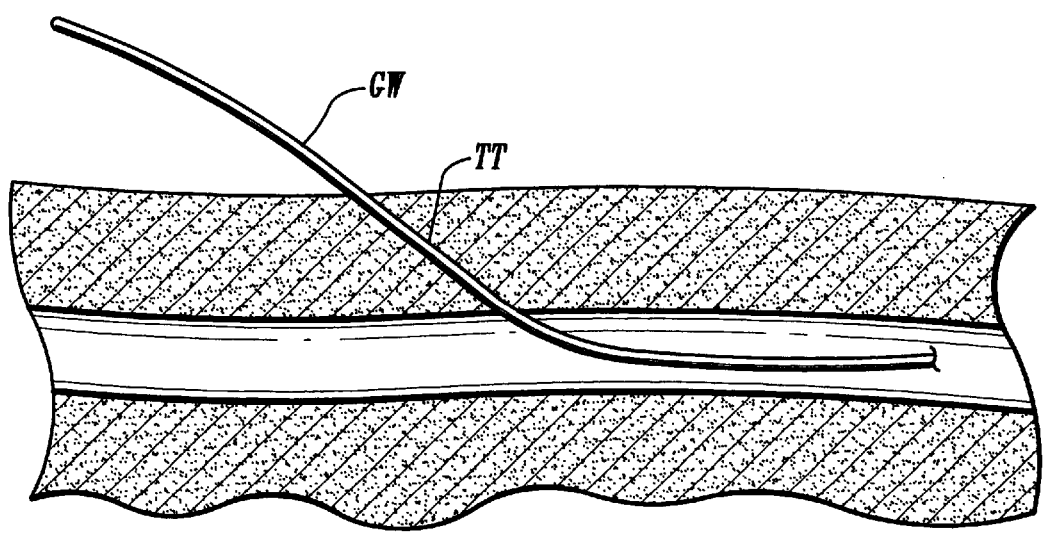
Figure 2C:
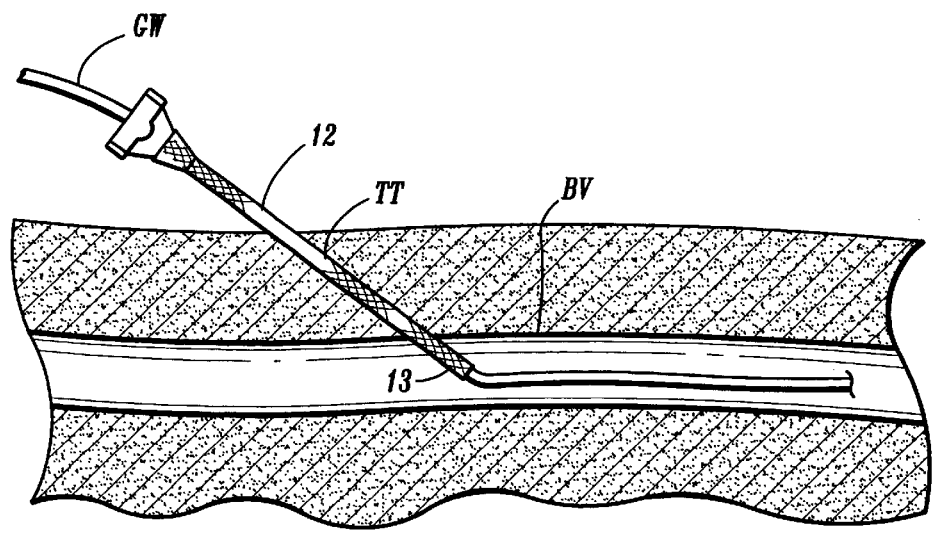
Figure 2D:
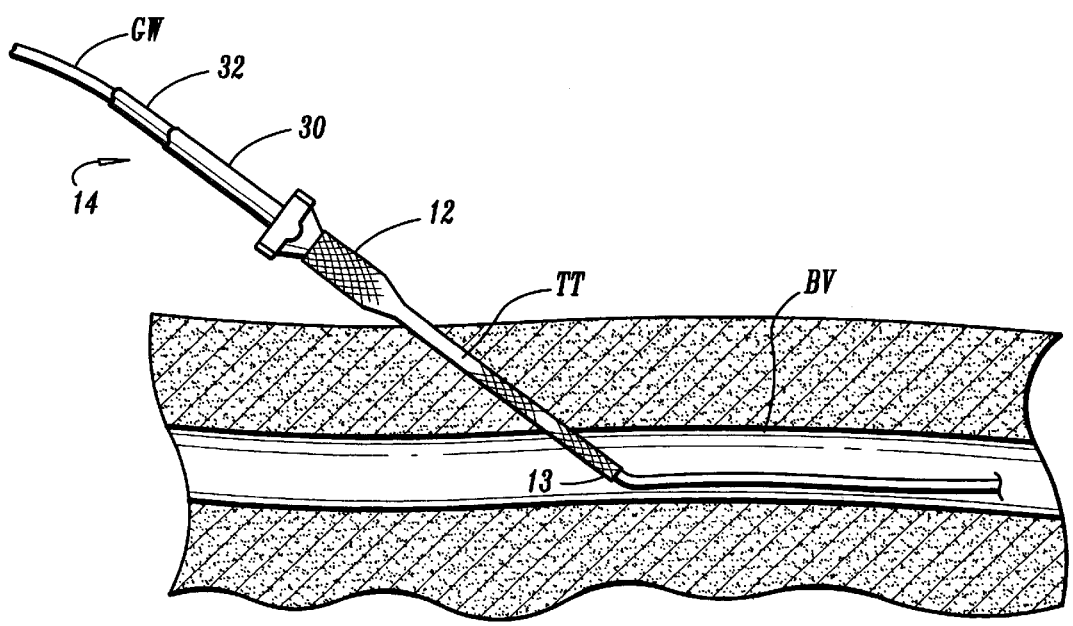
Figure 2E:
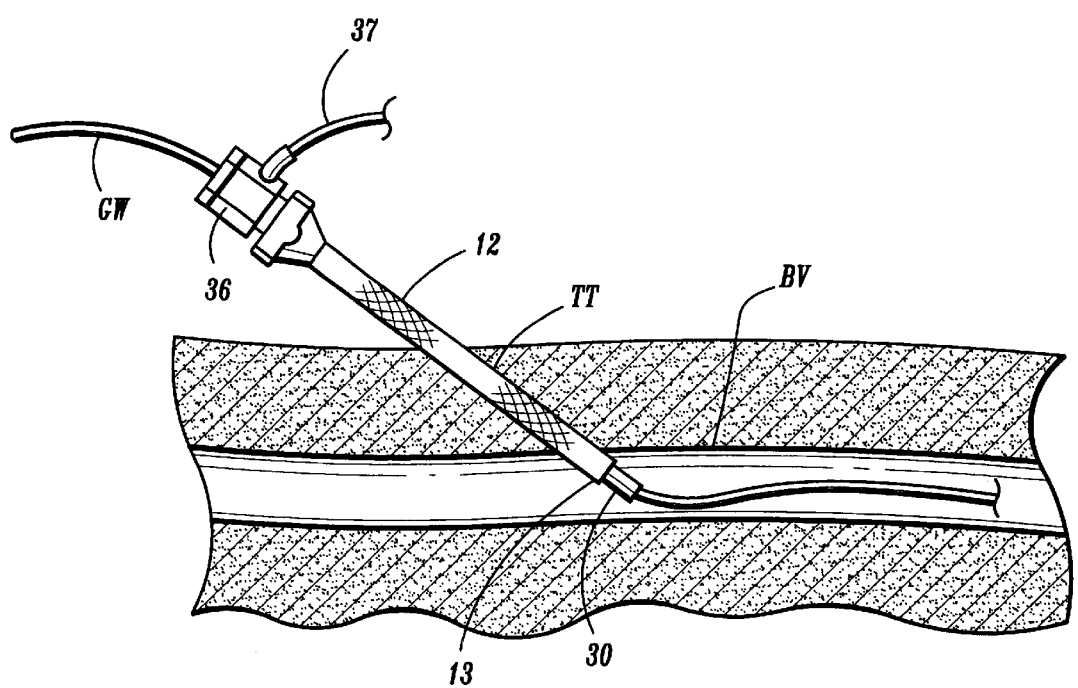

Referring now to FIGS. 2A–2E, use of the system 10 for accessing a blood vessel BV will be described. First, an initial tissue tract is formed using a needle N and syringe S assembly as shown in FIG. 2A. After access of the needle into the blood vessel BV is confirmed, typically by noting the flow of blood into the syringe S, the syringe may be removed and a guidewire GW placed through the needle into the blood vessel BV. The needle N may then be withdrawn over the proximal end of the guidewire GW, leaving the guidewire in place through a tissue tract TT, as illustrated in FIG. 2B. The radially expandable sleeve 12 is then introduced over the guidewire GW so that its distal end 13 lies within the blood vessel BV, as shown in FIG. 2C. The dilator 14 is then introduced over the guidewire GW so that the distal end of the dilator 14 causes radial expansion of the sleeve 12, as shown in FIG. 2D. After the dilator has been fully inserted through the sleeve 12, an inner dilator portion 32 may be withdrawn from the sheath 30, leaving the sheath in place through the radially expandable sleeve 12, both being over the guidewire GW, as shown in FIG. 2E. Vascular access has now been established for performing any one of a wide variety of diagnostic or therapeutic procedures as well described in the medical and patent literature.

Figure 3:
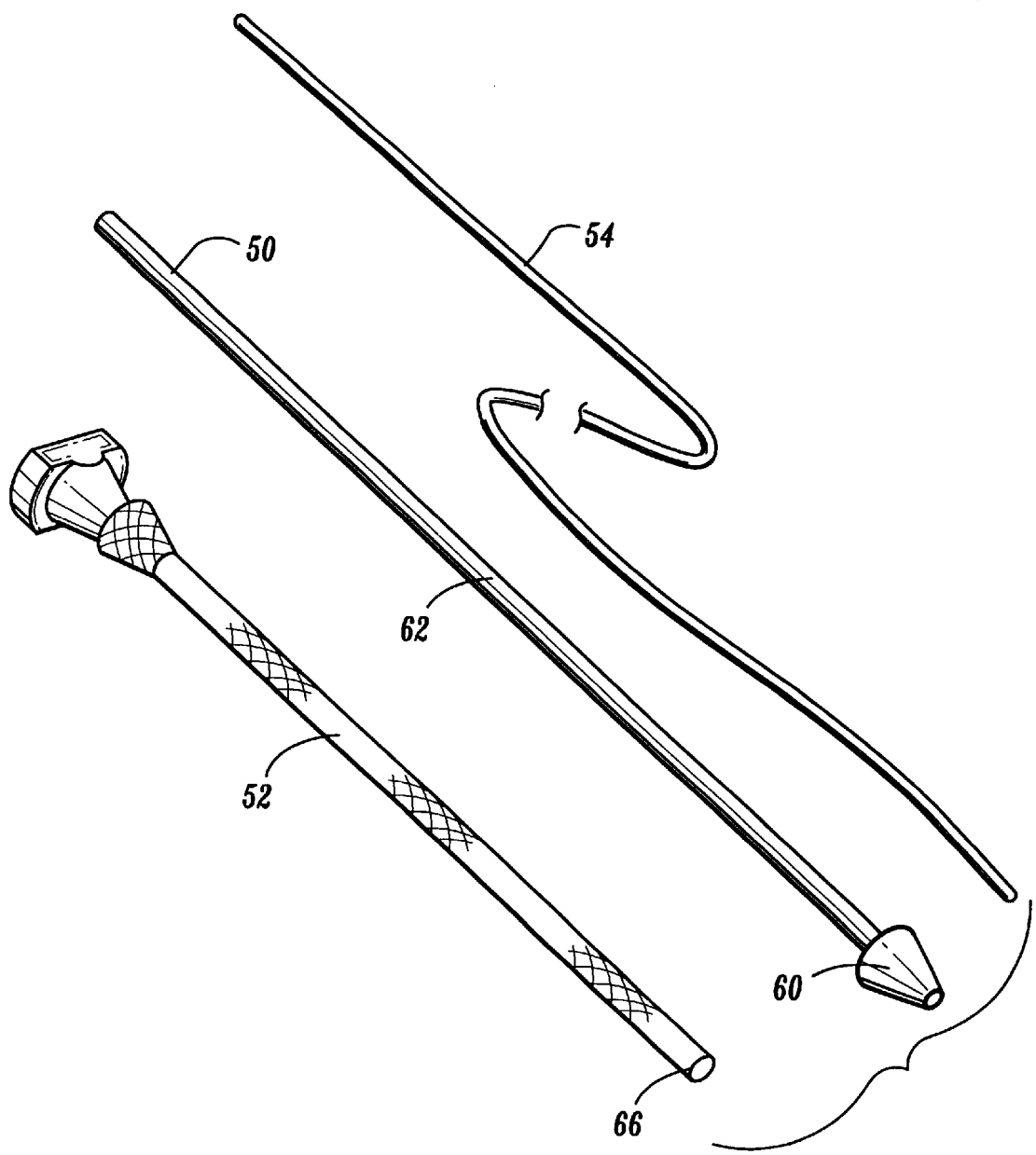
FIG. 3 illustrates a sleeve introducer which may combined in an assembly with a radially expandable sleeve and optionally a guidewire according to the systems and methods of the present invention.

Referring now to FIG. 3, a sleeve introducer 50 may be combined with a radially expandable sleeve 52 and optionally a guidewire 54 to form an expansible sleeve assembly intended for introduction through difficult tissue tracts, i.e., tissue tracts which might otherwise require excessive pushing force to introduce a sleeve according to the methods of the present invention. The sleeve introducer 50 comprises a tapered distal end 60, typically a conical element having a smaller diameter at its distal end and a larger diameter at its proximal end. The introducer 50 further comprises a shaft 62 extending proximally from the tapered distal end 60. The shaft will be a small tube, and the distal end 60 and shaft 62 together define a lumen which may be introduced over the guidewire 54. The outer diameter of the shaft 62 is selected so that it fits within the inner diameter of radially expandable sleeve 52. Preferably, the proximal end of the tapered distal end 60 will have a diameter which is the same as the outer diameter of the distal end 66 of the radially expandable sleeve 52. In this way, the sleeve introducer 50 may be placed within the lumen of the radially expandable sleeve 52 to form an assembly having a tapered distal end which facilitates introduction over the guidewire 54.

Figure 4A:
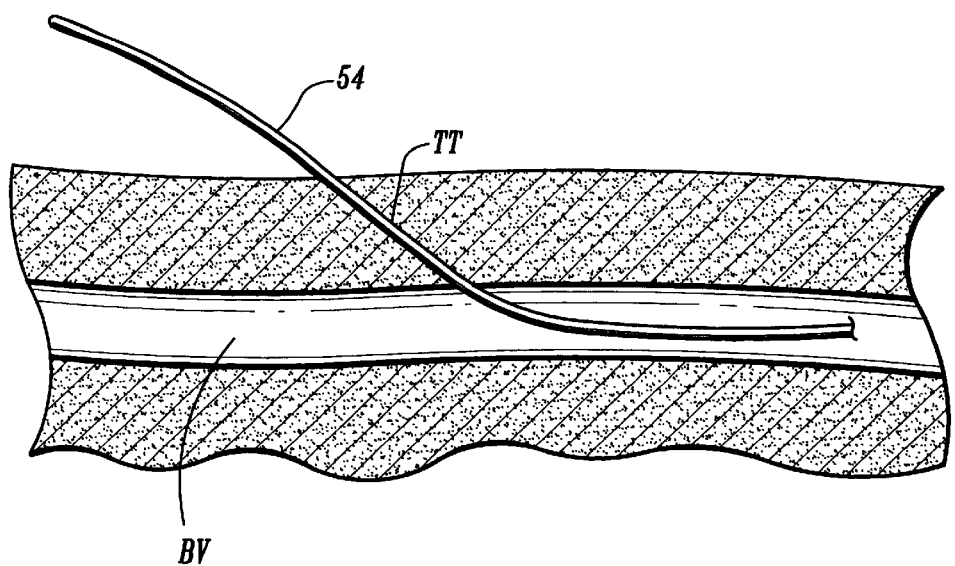
FIGS. 4A–4C illustrate use of the sleeve introducer assembly of FIG. 3 in the methods of the present invention.
Figure 4B:
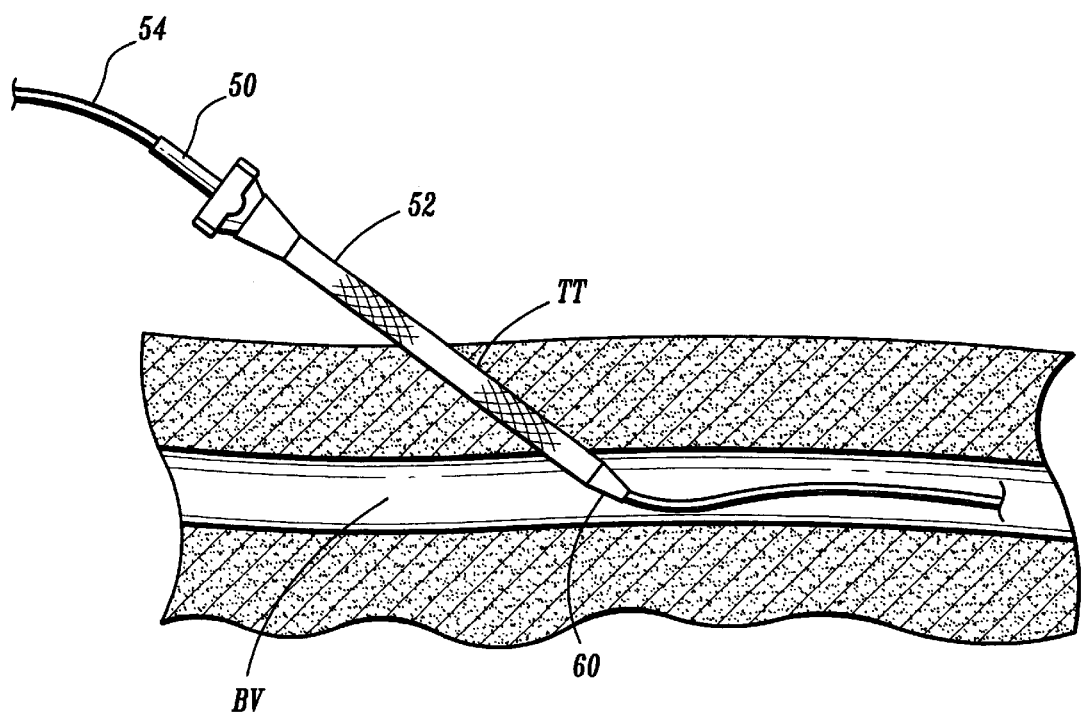
Figure 4C:
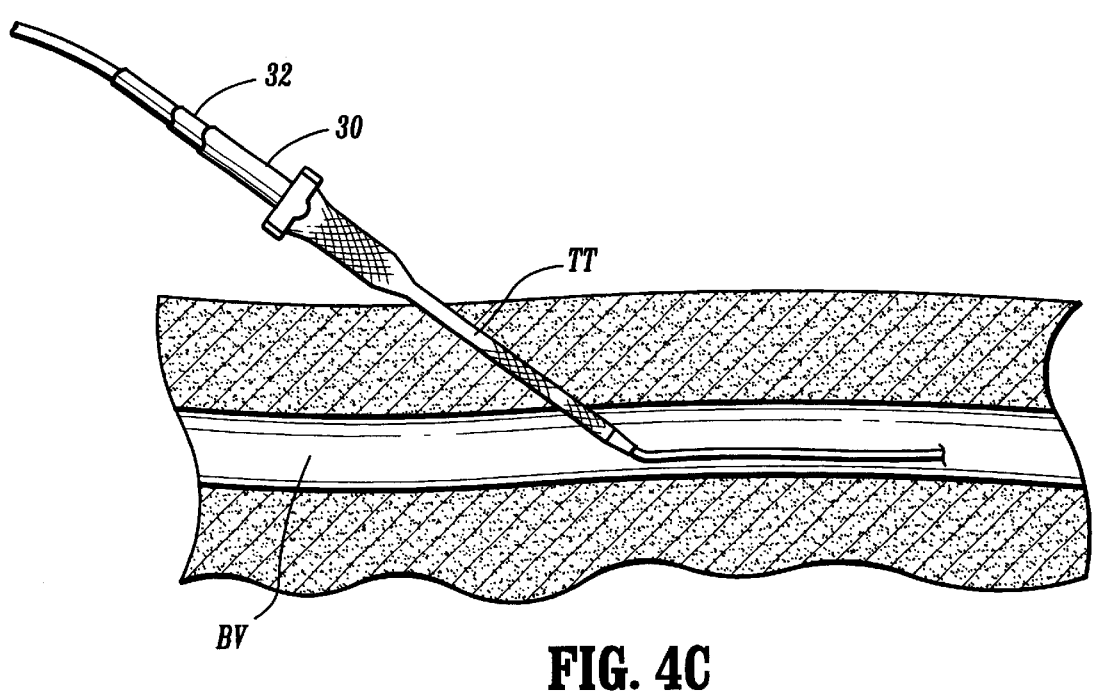

Referring now to FIGS. 4A–4C, use of the assembly of FIG. 3 for dilating the tissue tract to a blood vessel BV will be described. The guidewire 54 is first placed into the blood vessel BV, typically using a needle as described above in connection in FIG. 3A. Usually, the guidewire 54 used for more difficult introductions will have a slightly smaller diameter than would otherwise be necessary, such as a diameter of about 0.6 mm (0.025 in.). The assembly of the sleeve introducer 50 and radially expandable sleeve 52 is then introduced over the guidewire, with the guidewire passing directly through the lumen of the introducer 50. The tapered distal end 60 of the introducer 50 thus leads the way through the tissue over the guidewire 54, so that the taper facilitates passage of the assembly through the tissue. After the assembly is in place, as shown in FIG. 4B, a dilator 30 having an inner portion 32 may be introduced directly over the exterior of the sleeve introducer 50, as shown in FIG. 4C. After the tissue tract has been completely dilated, the combination of the sleeve introducer 50 and guidewire 54 may be withdrawn, leaving the inner diameter of the inner dilator portion 32 available for expanded access to the blood vessel BV.

Figure 5:
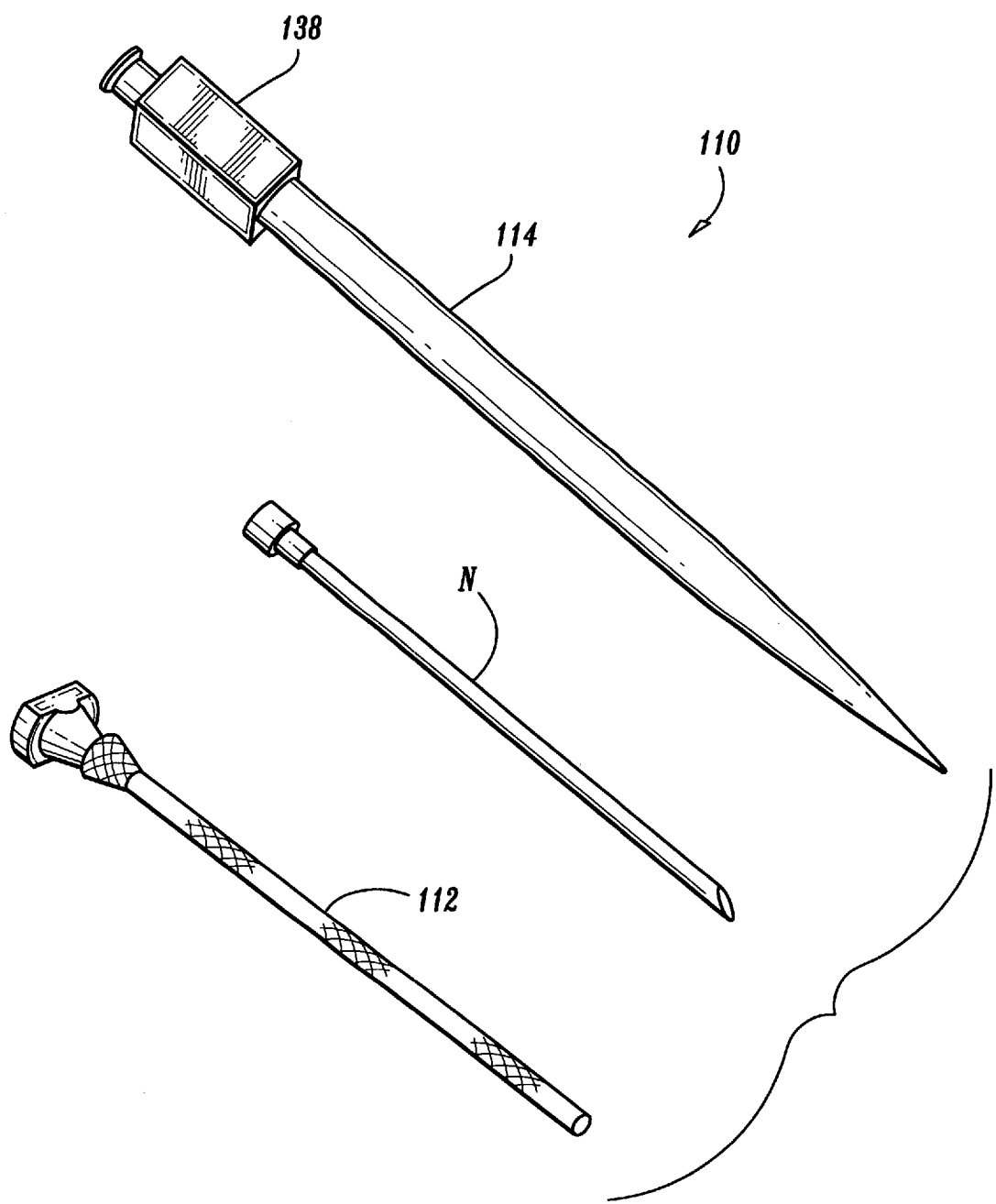
FIG. 5 illustrates a system comprising a radially expandable sleeve, a needle and a dilator, according to the present invention.

Alternatively, as shown in FIG. 5, a system 110 for establishing vascular access according to the principles of the present invention comprises a needle N, a radially expandable sleeve 112, and a dilator 114. The dilator 114 may be similar or identical to the dilator 14 previously described. However, in this case the dilator need not have a guidewire lumen. As previously illustrated, dilator 114 may be in the form of a conventional sheath/dilator assembly of the type which is commercially available from vendors, such as Bard Cardiology, Billerica, Mass., under the trade name Input™. The dilator/sheath assembly includes an outer sheath 130 with an inner tapered dilator 132 which is removable from the sheath. The sheath has a hemostatic valve 136 at its distal end and a side access tube 137 which permits perfusion or aspiration through the lumen of the sheath. The dilator 132 has a handle 138 at its proximal end. The dilator 114 shown in FIG. 5 is a conventional dilator, having a tapered distal end and a generally cylindrical body proximal to the distal end, without an associated access sheath. Such a dilator is suitable for use with or without an associated sheath.

The radially expandable sleeve 112 may be similar or identical to the sleeve 12 previously described and comprises a radially expandable tubular body having a proximal end, a distal end, and an axial lumen extending from the proximal end to the distal end. The expandable sleeve 112 may have a compliant or elastic structure which permits expansion from an initial small diameter (radially collapsed) configuration to a larger diameter configuration which is caused by introduction of the dilator 114 therethrough. Use of the compliant or elastic sleeve may require a separate component for maintaining the expanded diameter of the tissue tract. Such a component may be an access sheath associated with the dilator. In this case, the sleeve may contain a seal to prevent blood loss when the sheath is in place. As previously mentioned, the sheath itself may contain a hemostasis valve 136 preventing pressurized flow of blood within the blood vessel to escape through the sheath.

Alternatively, the radially expandable sleeve can have a plastic or other locking structure so that, once expanded, it will retain its large diameter configuration without the need for using other supports, devices, or the like, such as an access sheath. In this case, the sleeve itself would include a hemostasis valve 113 within its axial lumen. Such a valve will maintain a closed position when the dilator or other devices are removed from the sleeve, thus preventing the pressurized flow of blood within the blood vessel to escape through the sleeve. The valve will maintain an open position when activated, such as by the insertion of a catheter or other device through the valve. For example, a duckbill or miter valve would be particularly suitable.

Figure 6A:
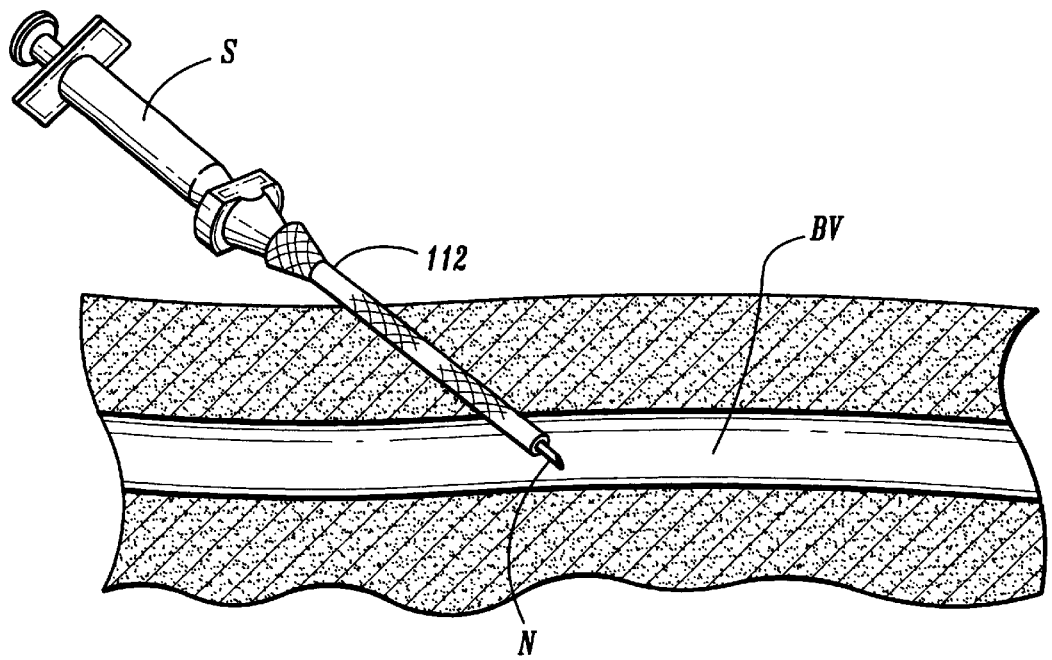
FIGS. 6A–6D illustrate use of the system of FIG. 5 for establishing vascular access to a target blood vessel according to a method of the present invention.
Figure 6B:
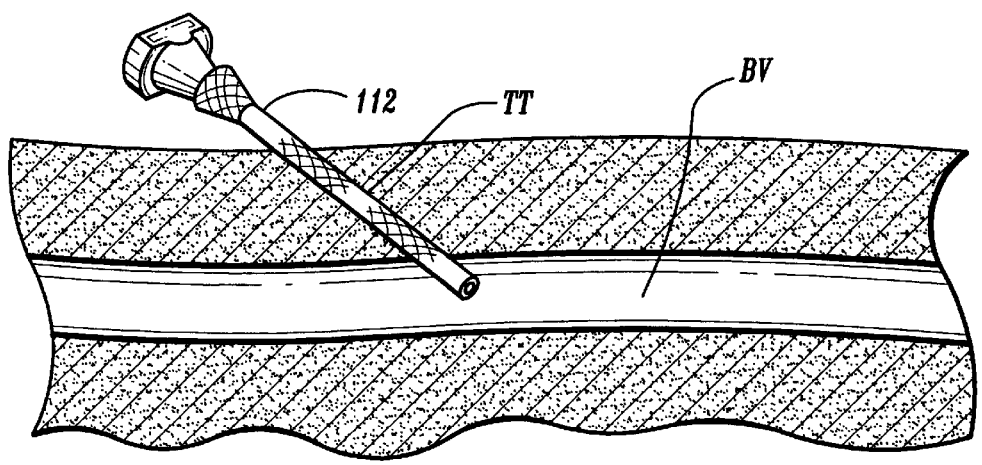
Figure 6C:
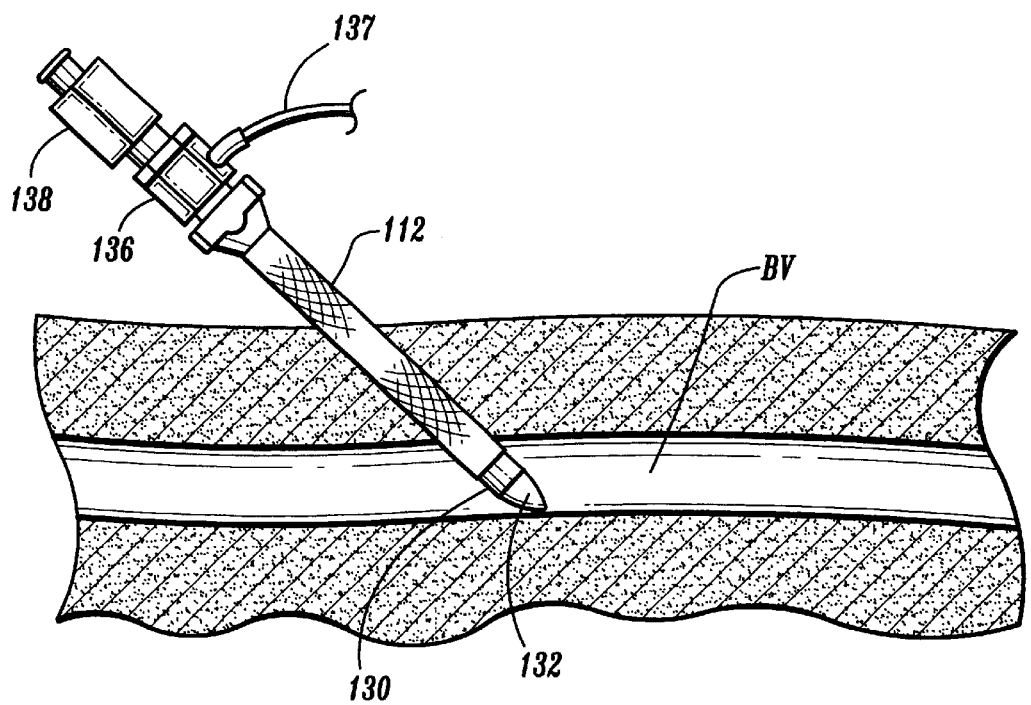
Figure 6D:
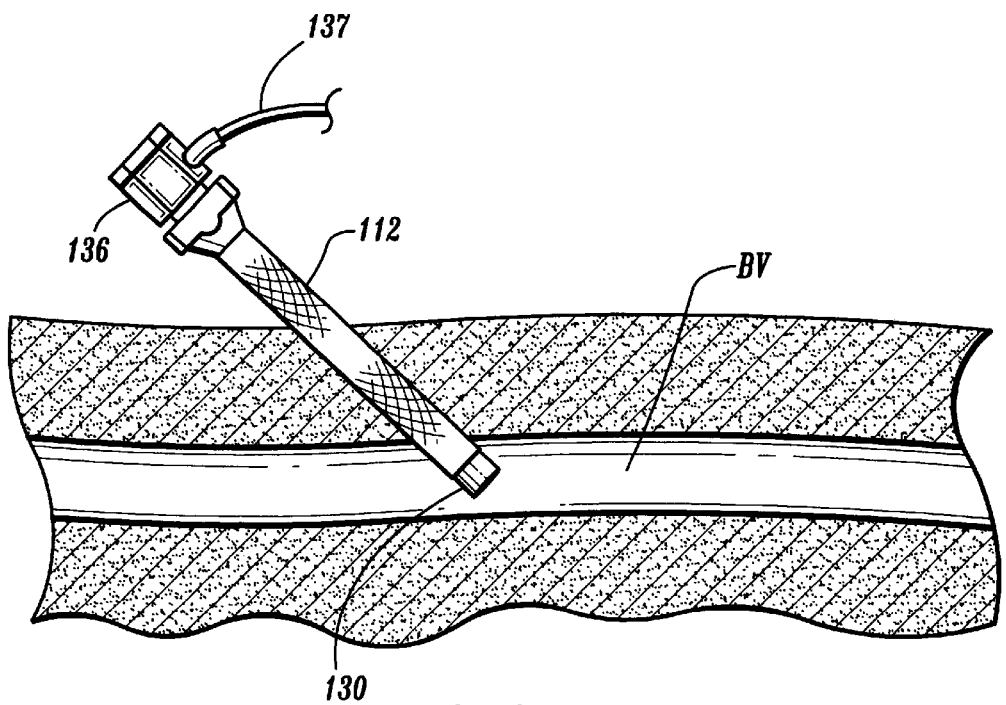

Referring now to FIGS. 6A–6C, use of the system 110 for accessing a blood vessel BV will be described. First, an initial tissue tract is formed using the expandable sleeve 112 mounted on an assembly comprising the needle N and a syringe S, as shown in FIG. 6A. After access of the needle into the blood vessel BV is confirmed, typically by noting the flow of blood into the syringe S, the needle/syringe assembly is withdrawn leaving the sleeve 112 in place through a tissue tract TT to the blood vessel BV, as illustrated in FIG. 6B. The sheath 130/dilator 132 assembly is then introduced through the sleeve 112 causing radial expansion of the sleeve 112, as shown in FIG. 6C. After the assembly has been fully inserted through the sleeve 112, the inner dilator portion 132 may be withdrawn from the sheath 130, leaving the sheath in place through the radially expandable sleeve 112, as shown in FIG. 6D. Vascular access has now been established for performing any one of a wide variety of diagnostic or therapeutic procedures as well described in the medical and patent literature.

Figure 7:
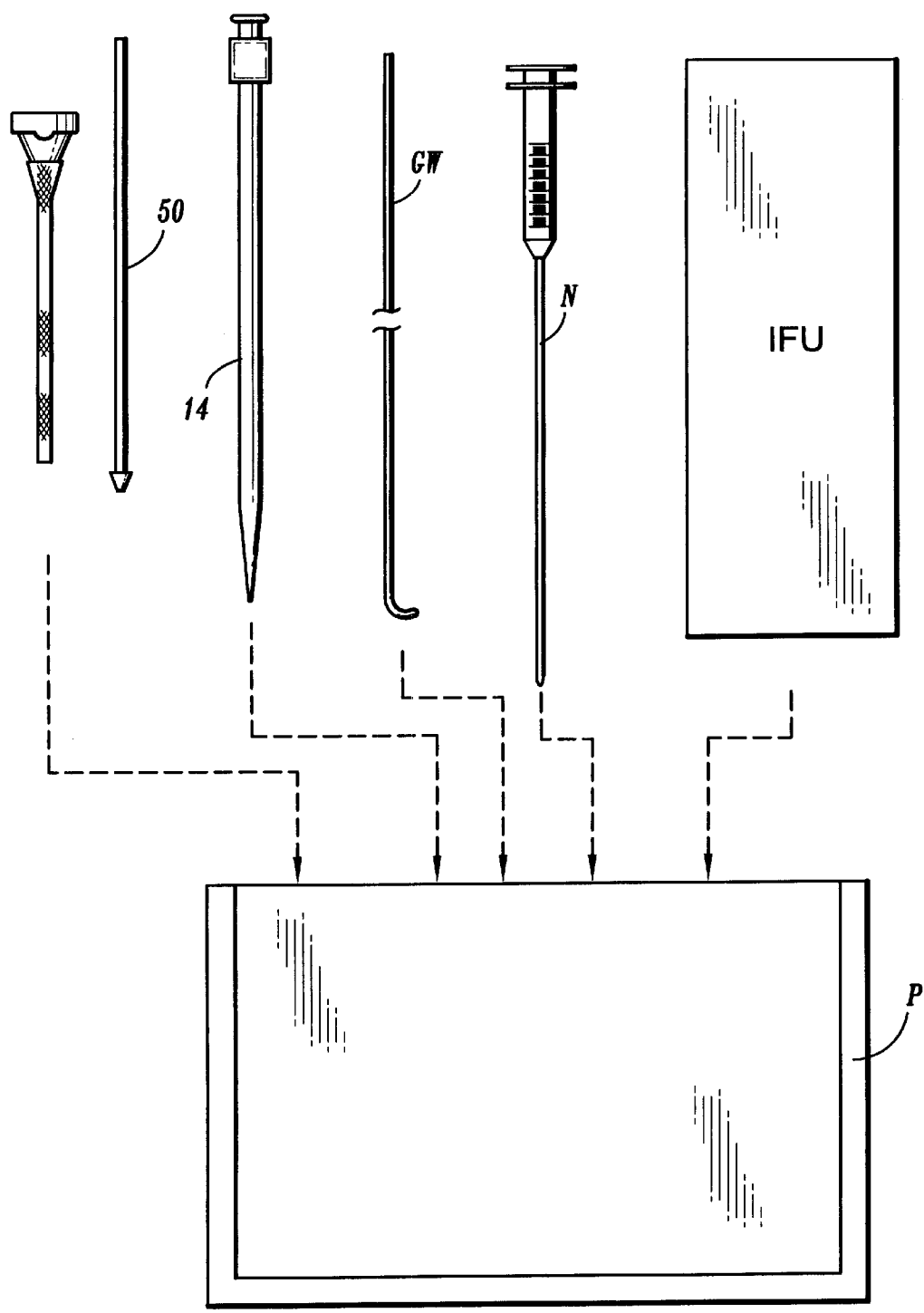
FIG. 7 illustrates a kit constructed in accordance with the principles of the present invention.

Referring now to FIG. 7, kits according to the present invention will comprise at least a radially expandable sleeve 12 or 112 together with instructions for use IFU setting forth any of the methods according to the principles of the present invention. Usually, a dilator 14 or 114 will also be included in the kit. The dilator 14 or 114 is shown as a simple dilator without an associated access sheath. Such a dilator is suitable for use with or without a sheath. The kits may optionally further comprise a guidewire GW, a sheath, a sleeve introducer 50, and/or a needle N and all kit components will typically be packaged together in a box, tray, tube, pouch, or other conventional medical device package P. The kit components which are employed in the medical procedure will typically be maintained within sterile packaging, with individual components being packaged either together or separately in different sterile containers. Usually, even when packaged in separate sterile containers, all components of the kit will be placed together within a common package. The instructions for use may be provided on a separate printed sheet, such as a conventional package insert, or may be printed in whole or in part on other portions of the packaging or the device itself.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for establishing vascular access, said method comprising the steps of:

inserting an access needle and a plastically deformable, radially expandable sleeve substantially simultaneously through a percutaneous tissue tract leading to a target blood vessel so that a distal end of the sleeve lies within the blood vessel and a proximal end of the sleeve lies outside the tissue tract, wherein the radially expandable sleeve has a compliant or elastic structure so that its cross-section will collapse after expansion;

expanding the expandable sleeve to a larger diameter configuration to provide an access lumen to the blood vessel; and locking said radially expandable sleeve to retain said larger diameter configuration.

2. A method as in claim 1, wherein the step of inserting includes penetrating the needle through tissue overlying the target blood vessel to form the tissue tract.

3. A method as in claim 2, wherein the sleeve is coaxially aligned with the needle so that insertion simultaneously positions both the needle and the sleeve.

4. A method as in claim 3, wherein the sleeve is coaxially mounted on the needle.

5. A method as in claim 4, wherein the sleeve has an outer diameter which is no more than 300% of the outer diameter of the needle.

6. A method as in claim 1, wherein the radially expandable sleeve comprises a tubular braid.

7. A method as in claim 6, wherein the tubular braid is a mesh of non-elastic filaments wherein radial expansion causes axial shortening of the braid.

8. A method as in claim 7, wherein the braid is embedded in or covered by an elastic layer.

9. A method as in claim 1, wherein the radially expandable sleeve comprises an anti-thrombotic coating.

10. A method as in claim 1, wherein the needle has a nominal diameter of 0.92 mm (0.036 in.), and the sleeve has a lumen diameter prior to expansion of 0.96 mm (0.038 in.).

11. A method for establishing vascular access said method comprising including the steps of:

inserting an access needle and a radially expandable sleeve substantially simultaneously through a percutaneous tissue tract leading to a target blood vessel, so that a distal end of the sleeve lies within the blood vessel and a proximal end of the sleeve lies outside the tissue tract, wherein the radially expandable sleeve includes a tubular braid which has a compliant or elastic structure and wherein the large diameter of the sleeve is maintained by an outer tube of the dilator which remains in place after the dilator is removed;

removing the needle from the tissue tract;

introducing a dilator through the expandable sleeve to increase the diameter of the expandable sleeve to a larger diameter;

removing the dilator wherein the expandable sleeve retains the larger diameter; and locking the radially expandable sleeve to retain said larger diameter.

12. A method as in claim 11, wherein the step of inserting includes penetrating the needle through tissue overlying the target blood vessel to form the tissue tract.

13. A method as in claim 12, wherein the sleeve is coaxially aligned with the needle so that insertion simultaneously positions both the needle and the sleeve.

14. A method as in claim 13, wherein the tubular braid is a mesh of non-elastic filaments wherein radial expansion causes axial shortening of the braid.

15. A method as in claim 14, wherein the braid is embedded in or covered by an elastic layer.

16. A method as in claim 11, wherein the radially expandable sleeve comprises an anti-thrombotic coating.

17. A method as in claim 11, wherein the sleeve has a lumen diameter prior to expansion of 0.96 mm (0.038 in.).

18. A method as in claim 17, wherein the dilator has an outside diameter in the range from 1.3 mm to 3.3 mm.

19. A method as in claim 11, wherein the sleeve has a lumen diameter prior to expansion of 0.41 mm (0.016 in.).

20. A method as in claim 19, wherein the dilator has an outside diameter in the range from 1 mm to 2.5 mm.

21. A method for establishing vascular access, said method comprising the steps of:

inserting an access needle and a plastically deformable, radially expandable sleeve substantially simultaneously through a percutaneous tissue tract leading to a target blood vessel so that a distal end of the sleeve lies within the blood vessel and a proximal end of the sleeve lies outside the tissue tract;

expanding the expandable sleeve to a larger diameter configuration to provide an access lumen to the blood vessel;

providing a locking structure to retain said expandable sleeve in said larger diameter configuration, said locking structure includes a valve disposed within said access lumen of said expandable sleeve;

locking said radially expandable sleeve to retain said larger diameter configuration.

22. The method as in claim 21, wherein said valve of said providing step is a hemostasis valve disposed within said access lumen.

23. The method as in claim 21, wherein said valve of said providing step is a duckbill valve.

24. The method as in claim 21, wherein said valve of said providing step is a miter valve.

25. The method as in claim 21, further including the steps of:

inserting a device through the valve; and maintaining the valve in an open position when the device is inserted through the valve.

26. A method for establishing vascular access, said method comprising the steps of:

positioning an access needle and a radially expandable sleeve through a percutaneous tissue tract leading to a target blood vessel so that a distal end of the sleeve lies within the blood vessel and a proximal end of the sleeve lies outside the tissue tract;

expanding the expandable sleeve to a larger diameter configuration to provide an access lumen to the blood vessel; and providing a locking structure to retain said expandable sleeve in said larger diameter configuration, said locking structure including a valve disposed within said access lumen of said expandable sleeve.

* * * * *